United States Patent [19]
Henrion et al.

[11] Patent Number: 5,873,910
[45] Date of Patent: Feb. 23, 1999

[54] PROCESS FOR THE TWO-STAGE OXIDATION DYEING OF KERATIN FIBERS WITH A MANGANESE COMPLEX OR SALT AND A 4-SUBSTITUTED 1-NAPHTHOL, AND DYEING KIT

[75] Inventors: Jean-Christophe Henrion, Pantin; Hervé Andrean, Paris, both of France

[73] Assignee: L'Oreal, Paris, France

[21] Appl. No.: 994,126

[22] Filed: Dec. 19, 1997

[30] Foreign Application Priority Data

Dec. 23, 1996 [FR] France .................................. 96 15893

[51] Int. Cl.⁶ ...................................................... A61K 7/13
[52] U.S. Cl. .......................... 8/406; 8/405; 8/404; 8/408; 8/411; 8/425; 8/409; 8/421; 8/435; 8/436; 8/412
[58] Field of Search ................................ 8/405, 406, 404, 8/408, 411, 425, 409, 421, 435, 436, 412

[56] References Cited

U.S. PATENT DOCUMENTS

| | | | |
|---|---|---|---|
| 2,001,992 | 5/1935 | Wagner et al. | 8/424 |
| 3,838,966 | 10/1974 | Barchas et al. | 8/405 |
| 5,061,289 | 10/1991 | Clausen et al. | 8/405 |
| 5,194,416 | 3/1993 | Jureller et al. | 502/167 |
| 5,534,267 | 7/1996 | Neunhoeffer et al. | 424/701 |

FOREIGN PATENT DOCUMENTS

| | | |
|---|---|---|
| 0 375 977 | 7/1990 | European Pat. Off. . |
| 758685 | 1/1934 | France . |
| 2 090 272 | 5/1971 | France . |
| 42 34 887 | 4/1994 | Germany . |
| 2 187 210 | 9/1987 | United Kingdom . |

*Primary Examiner*—Alan Diamond
*Attorney, Agent, or Firm*—Finnegan, Henderson, Farabow, Garrett & Dunner, L.L.P.

[57] ABSTRACT

A process for the two-stage oxidation dyeing of keratin fibers by applying to the keratin fibers:

in a first stage, at least one composition A containing at least one manganese salt and/or a manganese complex, in a second stage, at least one composition B having a pH of greater than or equal to 6, and resulting from the extemporaneous mixing of at least one composition B1 containing at least one 4-substituted 1-naphthol and at least one composition B2 containing at least one oxidizing agent, and corresponding multi-compartment dyeing kit.

37 Claims, No Drawings

PROCESS FOR THE TWO-STAGE OXIDATION DYEING OF KERATIN FIBERS WITH A MANGANESE COMPLEX OR SALT AND A 4-SUBSTITUTED 1-NAPHTHOL, AND DYEING KIT

The invention relates to a novel process for the two-stage oxidation dyeing of keratin fibers, and in particular human keratin fibers such as the hair, using, in a first stage, a manganese salt and/or a manganese complex, and, in a second stage, a 4-substituted 1-naphthol in an oxidizing medium having a pH of greater than or equal to 6.

The invention also relates to a multi-compartment device or "dyeing kit", intended to carry out the dyeing process according to the invention.

It has already been proposed, in particular in patent application FR-A-758,685, to dye animal fibers such as the skin, hairs, feathers and leather using dyes of 4-alkoxy-1-naphthol type, however, the dyeing conditions which are described in that document are not applicable to the dyeing of human hair since, according to that document, the dyeing is preferably carried out by impregnating the material to be dyed for several hours in a sodium hydroxide solution containing a 4-alkoxy-1-naphthol in the presence of an oxidizing agent. These drastic conditions are not cosmetically acceptable.

Moreover, it is well known that the oxidation of naphthols leads to the formation of pigments of the indigoid family in varied shades that are always sought in the sector of dyeing human keratin fibers such as the hair.

The dyeing of human keratin fibers must moreover satisfy a certain number of requirements. Thus, it must be free of toxicological drawbacks, it must allow shades to be obtained in the desired intensity and it must effectively withstand external agents (light, bad weather, washing, permanent waving, perspiration, rubbing).

The dyes must also be able to cover white hair and, lastly, they must be as unselective as possible, that is to say that they must allow only the smallest possible color differences along the same length of keratin fiber, which may indeed be differently sensitized (i.e., damaged) between its tip and its root.

The inventors have discovered that it is possible to obtain, quickly, particularly powerful and fast colorations with compounds of 4-substituted 1-naphthol type by applying, separately and spread out over time (in two stages), firstly, a composition A containing at least one manganese salt and/or at least one manganese complex, followed by a composition B having a pH of greater than or equal to 6 and resulting from the extemporaneous mixing (i.e., mixing just before use) of a composition B1 containing at least one compound of 4-substituted 1-naphthol type of formula (I) as defined below and a composition B2 containing at least one oxidizing agent.

This discovery forms the basis of the present invention.

The subject of the invention is thus a process for the two-stage oxidation dyeing of keratin fibers, and in particular human keratin fibers such as the hair, characterized in that:
in a first stage, at least one composition A containing, in a medium which is suitable for dyeing, at least one manganese salt and/or at least one manganese complex, and
in a second stage, at least one composition B having a pH of greater than or equal to 6, and resulting from the extemporaneous mixing of:
a) a composition B1 containing, in a medium which is suitable for dyeing, at least one 4-substituted 1-naphthol of formula (I) below:

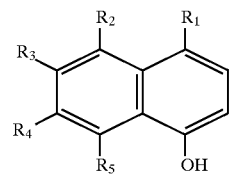

in which:
$R_1$ represents a halogen atom such as bromine, chlorine, iodine or fluorine; a benzyl radical; a benzyloxy radical; a linear, branched or cyclic $C_1$–$C_{29}$ alkoxy radical which may be substituted with one or more halogen atoms and/or interrupted by one or more hetero atoms; a $C_1$–$C_{29}$ acyloxy radical or a $C_1$–$C_{29}$ alkoxycarboxylic radical;
$R_2$, $R_3$, $R_4$ and $R_5$ independently represent a hydrogen atom, a halogen atom such as bromine, chlorine, iodine or fluorine or a hydroxyl, linear or branched $C_1$–$C_{29}$ alkyl, linear or branched $C_1$–$C_{29}$ alkoxy, acyl or benzyloxy radical, b) and a composition B2 containing, in a medium which is suitable for dyeing, at least one oxidizing agent, are applied to these fibers.

In formula (I) above, the alkyl, alkoxy and acyl radicals preferably have from 1 to 12 carbon atoms and even more preferably from 1 to 6 carbon atoms.

The colorations obtained according to the process of the invention are powerful and have excellent staying power with respect to the various treatments to which keratin fibers may be subjected. Furthermore, the oxidation dyeing process in accordance with the invention makes it possible to dye the keratin fibers quickly, under conditions that are entirely suited to cosmetic requirements, i.e., conditions which control all of the keratin fibers.

According to the process of the invention, the application of composition A to the fibers can be separated from the application of composition B to these same fibers by an intermediate towel-drying and/or rinsing step.

According to a particular and preferred embodiment of the process according to the invention, composition A is applied to the keratin fibers for an exposure time preferably ranging from approximately 5 seconds to approximately 10 minutes and even more preferably from approximately 30 seconds to approximately 5 minutes, after which composition B is applied to these fibers for an exposure time preferably from approximately 30 seconds to 45 minutes and even more preferably from approximately 3 minutes to approximately 30 minutes.

The manganese salt(s) which can be used in composition A according to the dyeing process of the invention have no intrinsic oxidizing activity and, in these salts, the manganese preferably has a degree of oxidation equal to 2 or 3. Needless to say, one or more manganese salts can be used.

These manganese salts are preferably selected from inorganic or organic, water-soluble manganese salts such as manganese dichloride, manganese trichloride, manganese sulphates, manganese nitrates, manganese diacetate, manganese carbonates, manganese dihydrogen carbonates, manganese acetylacetonate, manganese triacetate, manganese lactate, manganese formate, manganese acetylmethionate and manganese gluconate, and hydrates thereof.

The manganese complex(es) which can be used in composition A according to the dyeing process of the invention have no intrinsic oxidizing activity and are preferably selected from manganese complexes in which the manganese has a degree of oxidation equal to 4, such as those described, for example, in U.S. Pat. No. 5,194,416, the disclosure of which is specifically incorporated by reference herein. Among these manganese complexes, mention may be made more particularly of bis(octahydro-1,4,7-trimethyl-1H-1,4,7-triazinone-N1, N4, N7)tri-μ-oxodimanganese bis(hexafluorophosphate)

Manganese diacetate tetrahydrate and bis(octahydro-1,4,7-trimethyl-1H-1,4,7-triazinone-N1, N4, N7)tri-μ-oxodimanganese bis(hexafluorophosphate) are particularly preferred.

According to the invention, the manganese salt(s) and/or the manganese complex(es) is (are) preferably present in a concentration of ranging from approximately 0.0001 to approximately 1% by weight of metal equivalents relative to the total weight of composition A. Even more preferably, this concentration ranges from approximately 0.001 to approximately 0.15% by weight of metal equivalents relative to the total weight of composition A.

Among the compounds of formula (I) in accordance with the invention, mention may be made more particularly of:
4-benzylnaphth-1-ol,
4-chloronaphth-1-ol,
4-chloro-5,8-dimethoxy-6-methyinaphth-1-ol,
4-chloro-5,8-dimethoxynaphth-1-ol,
4-acetoxy-5-chloro-6-methyl-7-acetyl-8-hydroxynaphth-1-ol,
4-acetoxy-6-methyl-7-acetyl-8-hydroxynaphth-1-ol,
4-acetoxy-8-benzyloxynaphth-1-ol,
4-benzyloxynaphth-1-ol,
4,8-dibenzyloxy-6-methylnaphth-1-ol,
4,8-dibenzyloxynaphth-1-ol,
4-benzyloxy-8-(2-chloro)ethoxynaphth-1-ol,
4-benzyloxy-8-isopropyloxynaphth-1-ol,
4-benzyloxy-8-methoxynaphth-1-ol,
4-(2,2,2-trifluoroethoxy)naphth-1-ol,
4-(2-bromo)ethoxynaphth-1-ol,
4-(2-bromo)ethoxy-5-methoxynaphth-1-ol,
4-(2-bromo)ethoxy-8-methoxynaphth-1-ol,
4-(2-chloro)ethoxynaphth-1-ol,
4-(2-chloro)ethoxy-8-methoxynaphth-1-ol,
4-(2-methoxy)ethoxynaphth-1-ol,
4-(1,4,7-trioxaheptyl)naphth-1-ol,
4-(1,4,7-trioxaoctyl)naphth-1-ol,
4-(1,4,7,10-tetraoxadecyl)naphth-1-ol,
(4-hydroxy-1-naphthyl)oxyacetic acid,
4-methoxynaphth-1-ol,
4-methoxy-5-chloronaphth-1-ol,
4-methoxy-5-chloro-8-benzyloxynaphth-1-ol,
4,8-dimethoxy-5-chloronaphth-1-ol,
4-methoxy-5-methylnaphth-1-ol,
4-methoxy-5-benzyloxynaphth-1-ol,
4-methoxy-5-benzyloxy-7-methylnaphth-1-ol,
4-methoxy-5-hydroxynaphth-1-ol,
4-methoxy-5-hydroxy-7-methylnaphth-1-ol,
4-methoxy-5-isopropyloxynaphth-1-ol,
4,5-dimethoxynaphth-1-ol,
4,5-dimethoxy-6-benzyloxynaphth-1-ol,
4,5-dimethoxy-7-methyinaphth-1-ol,
4,5-dimethoxy-8-chloronaphth-1-ol,
4-methoxy-6-methyinaphth-1-ol,
4-methoxy-6-methyl-7-acetyl-8-hydroxynaphth-1-ol,
5- 4-methoxy-6,7-dimethylnaphth-1-ol,
4-methoxy-6-methyl-8-benzyloxynaphth-1-ol,
4-methoxy-6-methyl-8-hydroxynaphth-1-ol,
4,8-dimethoxy-6-methylnaphth-1-ol,
4-methoxy-6-ethoxynaphth-1-ol,
4-methoxy-6,7-diethoxynaphth-1-ol,
4-methoxy-7-methylnaphth-1-ol,
4,8-dimethoxy-7-benzyloxynaphth-1-ol,
4-methoxy-7-ethoxynaphth-1-ol,
4-methoxy-8-chloronaphth-1-ol,
4-methoxy-8-methyinaphth-1-ol,
4-methoxy-8-benzyloxynaphth-1-ol,
4-methoxy-8-hydroxynaphth-1-ol,
4-methoxy-8-isopropyloxynaphth-1-ol,
4,8-dimethoxynaphth-1-ol,
4-ethoxynaphth-1-ol,
4-propyloxynaphth-1-ol,
4-isopropyloxynaphth-1-ol,
4-butoxynaphth-1-ol,
4-isobutoxynaphth-1-ol,
4-sec-butoxynaphth-1-ol,
4-isoamoxynaphth-1-ol,
4-bis(2-chloroisopropyloxy)naphth-1-ol,
4-cyclohexyloxynaphth-1-ol,
4-octyloxynaphth-1-ol,
4-(2-chloropropoxy)naphth-1-ol,
isopropylidene-4,5-dioxynaphth-1-ol,
5-methoxynaphth-1-ol,
5,8-dimethoxy-6-methylnaphth-1-ol,
5,8-dimethoxy-6,7-dichloronaphth-1-ol,
5,8-dimethoxy-7-methyinaphth-1-ol,
5,8-diacetoxynaphth-1-ol, and
8-methoxynaphth-1-ol.

Among the compounds of formula (I) in accordance with the invention mentioned above,
4-methoxynaphth-1-ol,
4-ethoxynaphth-1-ol,
4-isopropyloxynaphth-1-ol, and
4,8-dimethoxynaphth-1-ol are most particularly preferred.

The compound(s) of formula (I) in accordance with the invention are present in a concentration preferably ranging from 0.001 to 5% by weight relative to the total weight of composition B1 and even more preferably from 0.01 to 2% by weight relative to the total weight of composition B1.

The pH of composition A generally ranges from approximately 3 to approximately 9, more preferably from approximately 6 to approximately 8 and even more preferably it is approximately equal to 7.

The pH of composition B must be greater than or equal to 6 and preferably ranges from 7 to 11.

Thus, the pH of compositions B1 and B2 is adjusted such that after mixing, just before use, of composition B1 with composition B2 in a weight ratio preferably ranging from 0.5 to 5 and even more preferably from 1 to 3, the pH of the resulting composition B is greater than or equal to 6 and preferably ranges from 7 to 11.

The pH of compositions A, B1, B2 and B can be adjusted to the desired value using basifying agents, or optionally acidifying agents, which are usually used for dyeing keratin fibers.

Among the basifying agents, mention may be made, by way of example, of aqueous ammonia, alkaline carbonates, alkanolamines such as mono-, di- and triethanolamine and derivatives thereof, sodium hydroxide, potassium hydroxide and compounds of formula (II) below:

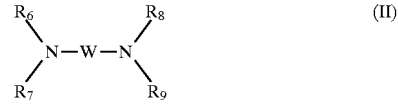

in which:
W is a propylene residue optionally substituted with a hydroxyl group or a $C_1$–$C_4$ alkyl radical;

$R_6$, $R_7$, $R_8$ and $R_9$ independently represent a hydrogen atom or a $C_1$–$C_4$ alkyl or $C_1$–$C_4$ hydroxyalkyl radical.

Among the acidifying agents, mention may be made, by way of example, of inorganic or organic acids such as hydrochloric acid, orthophosphoric acid, sulphuric acid, carboxylic acids such as acetic acid, tartaric acid, citric acid and lactic acid, and sulphonic acids.

According to a particular embodiment of the invention, composition B1 can contain, in addition to the compounds of formula (I) in accordance with the invention, one or more oxidation bases.

The optional oxidation base(s) is (are) selected from the oxidation bases used conventionally for the oxidation dyeing of keratin fibers, and are preferably selected from para-phenylenediamines, bis(phenyl)alkylenediamines, para-aminophenols, ortho-aminophenols and heterocyclic bases, and the acid-addition salts thereof.

When they are present, the oxidation base(s) are present in a concentration preferably ranging from approximately 0.001 to approximately 7% by weight, relative to the total weight of composition B1, and even more preferably from approximately 0.01 to approximately 2% by weight relative to the total weight of composition B1.

Composition B1 used according to the process of the invention can also contain one or more couplers and/or one or more direct dyes so as to vary the shades obtained with the compounds of formula (I) in accordance with the invention or to enrich them with glints.

The couplers which can be used in composition B1 used in the process in accordance with the invention can be selected from the couplers used conventionally in oxidation dyeing and, among which, mention may be made in particular of meta-phenylenediamines, meta-aminophenols, meta-diphenols and heterocyclic couplers such as, for example, indole derivatives and indolene ii derivatives, and the acid-addition salts thereof.

When they are present, these couplers are present in a concentration preferably ranging from approximately 0.001 to approximately 7% by weight, relative to the total weight of composition B1, and even more preferably from approximately 0.01 to approximately 2% by weight, relative to the total weight of composition B1.

The addition salts with an acid of the oxidation bases and/or of the couplers which can be used in composition B1 of the invention are selected, in particular, from the hydrochlorides, hydrobromides, sulphates, tartrates, lactates and acetates.

The oxidizing agent present in composition B2 as defined above can be selected from the oxidizing agents used conventionally for the oxidation dyeing of keratin fibers, and among which mention may be made of hydrogen peroxide, urea peroxide, iodates and periodates, metal oxides such as silver oxide, metal chlorides such as ferric chloride, ferric cyanide, alkali metal bromates, and persalts such as perborates and persulphates. Hydrogen peroxide at a concentration ranging from 0.03 to 100 volumes (i.e. from 0.01 to 30% by weight, relative to the total weight of composition B2) and even more preferably from 2 to 20 volumes (i.e. from 0.6 to 6% by weight) is preferably used.

The appropriate dyeing medium (or the support) for compositions A, B1 and B2 generally comprises water or of a mixture of water and at least one organic solvent in order to solubilize the compounds which would not be sufficiently water-soluble. By way of organic solvents, mention may be made, for example, of $C_1$–$C_4$ lower alkanols such as ethanol and isopropanol; glycerol; glycols and glycol ethers such as 2-butoxyethanol, propylene glycol, propylene glycol monomethyl ether and diethylene glycol monoethyl ether and monomethyl ether, and aromatic alcohols such as benzyl alcohol or phenoxyethanol, similar products and mixtures thereof.

The solvents may be present in a concentration preferably ranging from approximately 1 to approximately 40% by weight relative to the total weight of each composition in which they are contained, and even more preferably from approximately 5 to approximately 30% by weight, relative to the total weight of each composition in which they are contained.

Compositions A and/or B1 and/or B2, used according to the process in accordance with the invention, can also contain various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, fragrances, buffers, dispersants, conditioners such as, for example, silicones, film-forming agents, preserving agents and opacifiers.

Needless to say, a person skilled in the art will take care to select the optional complementary compound(s) mentioned above such that the advantageous properties intrinsically associated with the use according to the invention of compositions A, B1 and B2 are not, or are not substantially, adversely affected by the addition(s) envisaged.

Composition A used according to the process in accordance with the invention can be in the form of a relatively thickened liquid and in particular in the form of a lotion or a shampoo.

Composition B resulting from the extemporaneous mixing of compositions B1 and B2, which is used according to the process in accordance with the invention, can be in various forms, such as in the form of liquids, creams, gels or shampoos or in any other form which is suitable for dyeing keratin fibers, and in particular human hair.

Another subject of the invention is a multi-compartment dyeing device or "kit" or any other multi-compartment packaging system, a first compartment of which contains a composition A containing, in a medium which is suitable for dyeing, at least one manganese salt and/or at least one manganese complex, a second compartment of which contains a composition B1 containing, in a medium which is suitable for dyeing, at least one compound of formula (I) as defined above, and a third compartment of which contains a composition B2 containing, in a medium which is suitable for dyeing, at least one oxidizing agent as defined above, the pH of compositions B1 and B2 being adjusted such that after mixing composition B1 with composition B2 in a weight ratio preferably ranging from 0.5:1 to 5:1 and even more preferably from 1:1 to 3:1, the pH of the resulting composition B is preferably greater than or equal to 6 and more preferably ranges from 7 to 11. These devices can be equipped with a means which allows the desired mixture to be applied to the hair, such as the devices described in patent FR-2,586,913, the disclosure of which is specifically incorporated by reference herein.

The examples which follow are intended to illustrate the invention without, however, limiting its scope.

EXAMPLES

Dyeing Example 1

Compositions A, B1 and B2 below, in accordance with the invention, were prepared (contents in grams):

| Composition A: | |
|---|---|
| Bis(octahydro-1,4,7-trimethyl-1H-1,4,7-tri-azinone-N1,N4,N7)tri-$\mu$-oxodimanganese bis-(hexafluorophosphate) (manganese complex) | 0.001 g |
| Demineralized water q.s. | 100 g |

| Composition B1 | |
|---|---|
| Oleyl alcohol polyglycerolated with 2 mol of glycerol | 4.0 g |
| Oleyl alcohol polyglycerolated with 4 mol of glycerol, containing 78% active material (A.M.) | 5.69 g A.M. |
| Oleic acid | 3.0 g |
| Oleylamine containing 2 mol of ethylene oxide, sold under the trade name ETHOMEEN 012 by the company Akzo | 7.0 g |
| Diethylaminopropyl laurylaminosuccinamate, sodium salt, containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite as an aqueous solution containing 35% A.M. | 0.455 g A.M. |
| Ammonium acetate | 0.8 g |
| Antioxidant sequestering agent | q.s. |
| Fragrance, preserving agent | q.s. |
| Aqueous ammonia containing 20% NH$_3$ | 10.0 g |
| 4-Methoxynaphth-1-ol ($6 \times 10^{-3}$ mol) | 1.04 g |
| Demineralized water q.s. | 100.0 g |

Composition B2
20-Volumes hydrogen peroxide solution (6% by weight).

Composition A was applied to locks of natural grey hair containing 90% white hairs for 30 seconds, at a rate of 2 g of composition A per 1 g of hair to be treated, and the locks were then towel-dried.

Just before application, composition B1 was mixed weight-for-weight with the hydrogen peroxide solution B2, in order to obtain a composition B.

The resulting composition B was then applied to the locks of hair for 30 minutes. The hair was then rinsed, washed with shampoo and then dried.

The locks of hair were dyed in a blue shade.

Dyeing Examples 2 to 5

Compositions A, B1 and B2 below, in accordance with the invention, were prepared (contents in grams):

| Composition A: | |
|---|---|
| Bis(octahydro-1,4,7-trimethyl-1H-1,4,7-tri-azinone-N1,N4,N7)tri-$\mu$-oxodimanganese bis-(hexafluorophosphate) (manganese complex) | 0.001 g |
| Demineralized water q.s. | 100 g |

| Composition B1 | | | | |
|---|---|---|---|---|
| Example | 2 | 3 | 4 | 5 |
| 4-Methoxynaphth-1-ol | 1.04 | | | |
| 4-Ethoxynaphth-1-ol | | 1.13 | | |
| 4-Isopropyloxynaphth-1-ol | | | 1.21 | |
| 4,8-Dimethoxynaphth-1-ol | | | | 1.22 |
| Common dye support | (*) | (*) | (*) | (*) |

| Composition A: | | | | |
|---|---|---|---|---|
| Demineralized water | 100 g | 100 g | 100 g | 100 g |

(*) Common dye support:

| | |
|---|---|
| Benzyl alcohol | 10 g |
| $C_{16}$–$C_{18}$ Fatty alcohol | 8.9 g |
| Sodium ether sulphate of $C_{16}$–$C_{18}$ fatty alcohol | 8.9 g |
| Aqueous ammonia containing 20% NH$_3$ q.s. | pH = 10 |
| Demineralized water q.s. | 100 g |

Composition B2
20-Volumes hydrogen peroxide solution (6% by weight).

Composition A was applied to locks of natural grey hair containing 90% white hairs for 30 seconds, at a rate of 2 g of composition A per 1 g of hair to be treated, and the locks were then towel-dried.

Just before application, each composition B1 was mixed, weight-for-weight, with the hydrogen peroxide solution B2, in order to obtain the corresponding compositions B.

Each resulting composition B was then applied to the locks of hair for 30 minutes. The hair was then rinsed, washed with shampoo and then dried.

The locks of hair were dyed in the shades given in the table below:

| Example | Shade obtained |
|---|---|
| 2 | blue |
| 3 | blue |
| 4 | blue |
| 5 | orange-yellow |

Dyeing Examples 6 to 8

Compositions A, B1 and B2 below, in accordance with invention, were prepared (contents in grams):

| Composition A: | |
|---|---|
| Bis(octahydro-1,4,7-trimethyl-1H-1,4,7-tri-azinone-N1,N4,N7)tri-$\mu$-oxodimanganese bis-(hexafluorophosphate)(manganese complex) | 0.0001 g |
| Demineralized water q.s. | 100 g |

| Composition B1 | | | |
|---|---|---|---|
| Example | 6 | 7 | 8 |
| 4-Methoxynaphth-1-ol | 1.04 | 1.04 | 1.04 |
| 5-Amino-2-methylphenol | 0.369 | | 0.369 |
| Para-phenylenediamine | | 0.324 | 0.324 |
| Common dye support: | (*) | (*) | (*) |
| Demineralized water | 100 g | 100 g | 100 g |

(*) Common dye support:

| | |
|---|---|
| Benzyl alcohol | 10 g |
| $C_{16}$–$C_{18}$ Fatty alcohol | 8.9 g |
| Sodium ether sulphate of $C_{16}$–$C_{18}$ fatty alcohol | 8.9 g |
| Aqueous ammonia containing 20% NH$_3$ q.s. | pH = 10 |
| Demineralized water q.s. | 100 g |

Composition B2
20 Volumes hydrogen peroxide solution (6% by weight).

Composition A was applied to locks of natural grey hair containing 90% white hairs for 30 seconds, at a rate of 2 g of composition A per 1 g of hair to be treated, and the locks were then towel-dried.

Just before application, each composition B1 was mixed, weight-for-weight, with the hydrogen peroxide solution B2, in order to obtain the corresponding compositions B.

Each resulting composition B was then applied to the locks of hair for 30 minutes. The hair was then rinsed, washed with shampoo and then dried.

The locks of hair were dyed in the shades given in the table below:

| Example | Shade obtained |
|---|---|
| 6 | blue |
| 7 | intense plum |
| 8 | intense aubergine |

We claim:

1. A process for the two-stage oxidation dyeing of a keratin fiber, said process comprising:

in a first stage, applying to said keratin fiber at least one composition (A) containing, in a medium which is suitable for dyeing, at least one manganese salt and/or at least one manganese complex, and in a second stage, applying to said keratin fiber at least one composition B having a pH of greater than or equal to 6 and resulting from the extemporaneous mixing of:

a) a composition B1 containing, in a medium which is suitable for dyeing, at least one 4-substituted 1-naphthol of formula (I):

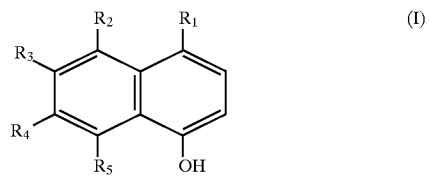

in which:

$R_1$ represents a halogen atom; a benzyl radical; a benzyloxy radical; a linear, branched or cyclic $C_1$–$C_{29}$ alkoxy radical which optionally is substituted with one or more halogen atoms and/or interrupted by one or more hetero atoms; a $C_1$–$C_{29}$ acyloxy radical or a $C_1$–$C_{29}$ alkoxycarboxylic radical;

$R_2$, $R_3$, $R_4$ and $R_5$ independently represent a hydrogen atom, a halogen atom, or a hydroxyl, linear or branched $C_1$–$C_{29}$ alkyl, linear or branched $C_1$–$C_{29}$ alkoxy, acyl or benzyloxy radical, and b) a composition B2 containing, in a medium which is suitable for dyeing, at least one oxidizing agent.

2. A process according to claim 1, wherein said keratin fiber is human hair.

3. A process according to claim 1, wherein $R_1$ is a halogen atom selected from bromine, chlorine, iodine and fluorine.

4. A process according to claim 1, wherein at least one of $R_2$, $R_3$, $R_4$ and $R_5$ independently represents a halogen atom selected from bromine, chlorine, iodine and fluorine.

5. A process according to claim 1, wherein said first stage, which comprises applying said at least one composition A to said keratin fiber, is separated from said second stage, which comprises applying said at least one composition B to said keratin fiber, by an intermediate towel-drying and/or rinsing step.

6. A process according to claim 1, wherein said at least one composition A is applied to said keratin fiber for an exposure time ranging from 5 seconds to 10 minutes, and said at least one composition B is applied to said keratin fiber for an exposure time ranging from 30 seconds to 45 minutes.

7. A process according to claim 6, wherein said exposure time for said at least one composition A ranges from 30 seconds to 5 minutes and said exposure time for said at least one composition B ranges from 3 to 30 minutes.

8. A process according to claim 1, wherein said composition A contains at least one manganese salt having no intrinsic oxidizing activity, and further wherein said manganese has a degree of oxidation equal to 2 or 3.

9. A process according to claim 8, wherein said at least one manganese salt is selected from organic and inorganic, water-soluble manganese salts.

10. A process according to claim 9, wherein said at least one manganese salt is selected from manganese dichloride, manganese trichloride, manganese sulphates, manganese nitrates, manganese diacetate, manganese carbonates, manganese dihydrogen carbonates, manganese acetylacetonate, manganese triacetate, manganese lactate, manganese formate, manganese acetylmethionate and manganese gluconate, and hydrates thereof.

11. A process according to claim 1, wherein said composition A contains at least one manganese complex having no intrinsic oxidizing activity and further wherein said manganese has a degree of oxidation equal to 4.

12. A process according to claim 11, wherein said at least one manganese complex is bis(octahydro-1,4,7-trimethyl-1H-1,4,7-triazinone-N1, N4, N7)tri-$\mu$-oxodimanganese bis (hexafluorophosphate).

13. A process according to claim 1, wherein said at least one manganese salt and/or at least one manganese complex are present in a concentration ranging from 0.0001 to 1% by weight of metal equivalents relative to the total weight of composition A.

14. A process according to claim 13, wherein said at least one manganese salt and/or at least one manganese complex are present in a concentration ranging from 0.001 to 0.15% by weight of metal equivalents relative to the total weight of composition A.

15. A process according to claim 1, wherein said at least one 4-substituted 1-naphthol of formula (I) is selected from:
4-benzylnaphth-1-ol,
4-chloronaphth-1-ol,
4-chloro-5,8-dimethoxy-6-methylnaphth-1-ol,
4-chloro-5,8-dimethoxynaphth-1-ol,
4-acetoxy-5-chloro-6-methyl-7-acetyl-8-hydroxynaphth-1-ol,
4-acetoxy-6-methyl-7-acetyl-8-hydroxynaphth-1-ol,
4-acetoxy-8-benzyloxynaphth-1-ol,
4-benzyloxynaphth-1-ol,
5- 4,8-dibenzyloxy-6-methylnaphth-1-ol,
4,8-dibenzyloxynaphth-1-ol,
4-benzyloxy-8-(2-chloro)ethoxynaphth-1-ol,
4-benzyloxy-8-isopropyloxynaphth-1-ol,
4-benzyloxy-8-methoxynaphth-1-ol,
4-(2,2,2-trifluoroethoxy)naphth-1-ol,
4-(2-bromo)ethoxynaphth-1-ol,
4-(2-bromo)ethoxy-5-methoxynaphth-1-ol,
4-(2-bromo)ethoxy-8-methoxynaphth-1-ol,
4-(2-chloro)ethoxynaphth-1-ol,
4-(2-chloro)ethoxy-8-methoxynaphth-1-ol,
4-(2-methoxy)ethoxynaphth-1-ol,
4-(1,4,7-trioxaheptyl)naphth-1-ol,
4-(1,4,7-trioxaoctyl)naphth-1-ol,
4-(1,4,7,1 0-tetraoxadecyl)naphth-1-ol,
(4-hydroxy-1-naphthyl)oxyacetic acid,
4-methoxynaphth-1-ol,
4-methoxy-5-chloronaphth-1-ol,
4-methoxy-5-chloro-8-benzyloxynaphth-1-ol,
4,8-dimethoxy-5-chloronaphth-1-ol,
4-methoxy-5-methylnaphth-1-ol,
4-methoxy-5-benzyloxynaphth-1-ol, 4-methoxy-5-benzyloxy-7-methyinaphth-1-ol,
4-methoxy-5-hydroxynaphth-1-ol,
4-methoxy-5-hydroxy-7-methylnaphth-1-ol,
4-methoxy-5-isopropyloxynaphth-1-ol,
4,5-dimethoxynaphth-1-ol,
4,5-dimethoxy-6-benzyloxynaphth-1-ol,
4,5-dimethoxy-7-methylnaphth-1-ol,
4,5-dimethoxy-8-chloronaphth-1-ol,
4-methoxy-6-methylnaphth-1-ol,
4-methoxy-6-methyl-7-acetyl-8-hydroxynaphth-1-ol,
4-methoxy-6,7-dimethylnaphth-1-ol,
4-methoxy-6-methyl-8-benzyloxynaphth-1-ol,
4-methoxy-6-methyl-8-hydroxynaphth-1-ol,
4,8-dimethoxy-6-methylnaphth-1-ol,
4-methoxy-6-ethoxynaphth-1-ol,
4-methoxy-6,7-diethoxynaphth-1-ol,
4-methoxy-7-methylnaphth-1-ol,
4,8-dimethoxy-7-benzyloxynaphth-1-ol,
4-methoxy-7-ethoxynaphth-1-ol,
4-methoxy-8-chloronaphth-1-ol,
4-methoxy-8-methyinaphth-1-ol,
4-methoxy-8-benzyloxynaphth-1-ol,
4-methoxy-8-hydroxynaphth-1-ol,
4-methoxy-8-isopropyloxynaphth-1-ol,
4,8-dimethoxynaphth-1-ol,
4-ethoxynaphth-1-ol,
4-propyloxynaphth-1-ol,
4-isopropyloxynaphth-1-ol,
4-butoxynaphth-1-ol,
4-isobutoxynaphth-1-ol,
4-sec-butoxynaphth-1-ol,
4-isoamoxynaphth-1-ol,
4-bis(2-chloroisopropyloxy)naphth-1-ol,
4-cyclohexyloxynaphth-1-ol,
4-octyloxynaphth-1-ol,
4-(2-chloropropoxy)naphth-1-ol,
isopropylidene-4,5-dioxynaphth-1-ol,
5-methoxynaphth-1-ol,
5,8-dimethoxy-6-methyinaphth-1-ol,
5,8-dimethoxy-6,7-dichloronaphth-1-ol,
5,8-dimethoxy-7-methylnaphth-1-ol,
5,8-diacetoxynaphth-1-ol, and
8-methoxynaphth-1-ol.

16. A process according to claim 15, wherein said at least one 4-substituted 1-naphthol of formula (I) is selected from:
4-methoxynaphth-1-ol,
4-ethoxynaphth-1-ol,
4-isopropyloxynaphth-1-ol, and
4,8-dimethoxynaphth-1-ol.

17. A process according to claim 1, wherein said at least one 4-substituted 1-naphthol of formula (I) is present in a concentration ranging from 0.001 to 5% by weight relative to the total weight of composition B1.

18. A process according to claim 17, wherein said at least one 4-substituted 1-naphthol of formula (I) is present in a concentration ranging from 0.01 to 2% by weight relative to the total weight of composition B1.

19. A process according to claim 1, wherein the pH of said at least one composition A ranges from 3 to 9.

20. A process according to claim 19, wherein the pH of said at least one composition A ranges from 6 to 8.

21. A process according to claim 20, wherein the pH of said at least one composition A is approximately equal to 7.

22. A process according to claim 1, wherein the pH of said at least one composition B is greater than or equal to 6.

23. A process according to claim 22, wherein the pH of said at least one composition B ranges from 7 to 11.

24. A process according to claim 1, wherein said at least one composition B1 further comprises at least one oxidation base or an acid-addition salt thereof and/or at least one coupler or an acid-addition salt thereof, and/or at least one direct dye.

25. A process according to claim 24, wherein said at least one oxidation base is present in a concentration ranging from 0.001 to 7% by weight, relative to the total weight of composition B1.

26. A process according to claim 24, wherein said at least one coupler is present in a concentration ranging from 0.001 to 7% by weight, relative to the total weight of composition B1.

27. A process according to claim 24, wherein said acid-addition salt is selected from hydrochlorides, hydrobromides, sulphates, tartrates, lactates and acetates.

28. A process according to claim 1, wherein said at least one oxidizing agent present in said composition B2 is selected from hydrogen peroxide, urea peroxide, iodates and periodates, metal oxides, metal chlorides, ferric cyanide, alkali metal bromates, and persalts.

29. A process according to claim 28, wherein said persalts are selected from perborates and persulphates.

30. A process according to claim 28, wherein said at least one oxidizing agent is hydrogen peroxide.

31. A process according to claim 30, wherein said hydrogen peroxide is present in a concentration ranging from 0.01 to 30% by weight, relative to the total weight of said composition B2.

32. A process according to claim 1, wherein said medium suitable for dyeing comprises water or a mixture of water and at least one organic solvent selected from $C_1$–$C_4$ lower alkanols, glycerol, glycols, glycol ethers, and aromatic alcohols.

33. A process according to claim 1, wherein said at least one composition A is in the form of a thickened liquid.

34. A process according to claim 33, wherein said at least one composition A is in the form of a lotion or shampoo.

35. A process according to claim 1, wherein said at least one composition B is in the form of a liquid, cream, gel, shampoo, or any other form suitable for dyeing human keratin fibers.

36. A multi-compartment device or multi-component dyeing kit, comprising:
(a) a first compartment comprising composition A containing, in a medium which is suitable for dyeing, at least one manganese salt and/or at least one manganese complex,
(b) a second compartment comprising composition B1 containing, in a medium which is suitable for dyeing, at least one compound of formula (I);

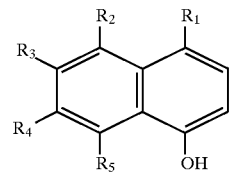

in which:
$R_1$ represents a halogen atom; a benzyl radical; a benzyloxy radical; a linear, branched or cyclic $C_1$–$C_{29}$ alkoxy radical which optionally is substituted with one or more halogen atoms and/or interrupted by one or more hereto atoms; a $C_1$–$C_{29}$ acyloxy radical or a $C_1$–$C_{29}$ alkoxycarboxylic radical;

$R_2$, $R_3$, $R_4$, and $R_5$ independently represent a hydrogen atom, a halogen atom, or a hydroxy, linear or branched $C_1$–$C_{29}$ alkyl, linear or branched $C_1$–$C_{29}$ alkoxy, acyl or benzyloxy radical, and (c) a third compartment comprising composition B2 containing, in a medium which is suitable for dyeing, at least one oxidizing agent, wherein the pH of the mixture of said composition B1 and said composition B2 in a weight ratio ranging from 0.5:1 to 5:1, is greater than or equal to 6.

37. A multi-compartment device or multi-compartment dyeing kit according to claim 36, wherein said weight ratio of said mixture of said composition B1 and said composition B2 ranges from 1:1 to 3:1.

* * * * *

UNITED STATES PATENT AND TRADEMARK OFFICE
CERTIFICATE OF CORRECTION

PATENT NO. : 5,873,910
DATED : February 23, 1999
INVENTOR(S) : Jean-Christophe HENRION et al.

It is certified that error appears in the above-identified patent and that said Letters Patent is hereby corrected as shown below:

In the Claims: Claim 15, col. 10, line 46, delete "5-";

Claim 15, col. 10, line 60, change "1 0" to --10--; and

Claim 15, col. 11, line 39, change "methyinapth" to --methylnapth--.

Signed and Sealed this

Third Day of August, 1999

Attest:

Q. TODD DICKINSON

Attesting Officer

Acting Commissioner of Patents and Trademarks